United States Patent [19]

La Gamma

[11] Patent Number: 6,162,426
[45] Date of Patent: Dec. 19, 2000

[54] USE OF G-CSF TO ENHANCE THE IMMUNE SYSTEM IN NEONATES

[76] Inventor: Edmund F. La Gamma, 2 Ledgewood Cir., Setauket, N.Y. 11733

[21] Appl. No.: 08/851,044

[22] Filed: May 5, 1997

[51] Int. Cl.$^7$ .................................................. A61K 45/00
[52] U.S. Cl. ................................. 424/85.1; 514/2; 514/8; 514/12; 514/885
[58] Field of Search ............................... 424/85.1; 514/2, 514/8, 12, 885

[56] References Cited

U.S. PATENT DOCUMENTS

| | | | |
|---|---|---|---|
| 4,810,643 | 3/1989 | Souza | 435/68 |
| 5,536,495 | 7/1996 | Foster | 424/851 |

OTHER PUBLICATIONS

Gillan et al. Blood, vol. 84, No. 5, pp. 1427–1433, 1994.
Cunningham et al. (1989) Science vol. 244, pp. 1081–1085, 1989.
George et al. (1988) Macromolecular Sequencing & Synthesis pp. 127–149, Alan B. Liss, Inc., 1988.
R. Roberts, C. Szelc, S. Scates, M. Boyd, K. Soderstrom, M. Davis, J. Glapsy, "Neutropenia in an Extremely Premature Infant Treated With Recombinant Human Granulocyte Colony–Stimulating Factor," AJDC–vol. 145, Jul. 1991, pp. 808–812.
Pediatic Research, Program Issue APS–SPR, "Human Granulocyte Colony Stimulating Factor (rhG–CSF) May Improve Outcome Due to Neonatal Sepsis Complicated by Neutropenia," Apr. 1997, vol. 41, No. 4, Part 2, P. Kocherlakota et al.
Pediatric Research, Program Issue APS–SPR, "Neonatal Immunology And Hematology" Apr. 1996, vol. 39, No. 4, Part 2, P. Kocherlakota et al.
P. Kocherlakota, E.F. LaGamma, C. Breen, H.B. Fleit, M. Golightly, "Effects of rhG–CSF on Neutrophil Fcy and Complement Receptors in Ventilated Very Low Birth Weight Human Neonates" Neonatal Hematology & Immunology III (1997) pp. 39–48.
"The Use of Granulocyte Colony Stimulating Factro (G–CSF) for Prophylaxis of Neonatal Sepsis," Annual Report: 1996 (Period: Jan. 1996–Mar. 1997) Phase I Trial BB–IND No. 5616–001, pp. 2–10.
La Gamma et al. (1995) J. of Pediatrics, vol. 126, No. 3, pp. 457–459.

*Primary Examiner*—Prema Mertz
*Attorney, Agent, or Firm*—Proskauer Rose LLP

[57] ABSTRACT

The invention relates to the use of Granulocyte Colony Stimulating Factor (G-CSF) to enhance the immune system in neonates by increasing the Absolute Neutrophil Count and/or increasing the $Fc_\gamma$ receptor density on the surface of neutrophils in neonates. More particularly, the invention relates to the use of G-CSF to enhance neutrophil production and/or $Fc_\gamma$ receptor density in very Low Birth Weight (VLBW) neonates, pre-eclamptic neutropenic neonates, and septic-neutropenic neonates. The invention also includes the use of G-CSF in association with IUGG to enhance opsonziation of infectious organisms either by prophylaxis or as a therapeutic intervention.

4 Claims, 1 Drawing Sheet

USE OF G-CSF TO ENHANCE THE IMMUNE SYSTEM IN NEONATES

FIELD OF THE INVENTION

This invention relates to the use of Granulocyte Colony-Stimulating Factor (G-CSF) to stimulate the immune system in neonates. Particularly, the invention relates to the use of G-CSF in Very Low Birth Weight (VLBW; <1500 g at birth), Pre-eclamptic Neutropenic, and Septic-Neutropenic neonates in order to stimulate the production of receptors on the surface of neutrophils and/or to increase the absolute neutrophil count in neonates suffering from these conditions.

BACKGROUND OF THE INVENTION

Neonatal bacterial infection is a major cause of morbidity in the United States today. Bacterial infections are even more dangerous for neonates who are Very Low Birth Weight (VLBW) since the immune system of these neonates is severely compromised. The overall immune system of neonates has several components each of which work to complement one another. The two major components of the overall immune system in neonates are the neutrophil-macrophage phagocytic system and the antibody-mediated immunity system. In a healthy neonate these systems are able to protect the neonate against bacterial and viral infections. However, in a neonate in which these systems are compromised the likelihood of bacterial or viral infection is extremely high and usually results in death.

The neutrophil-macrophage phagocytic system utilizes neutrophils, the chief phagocytotic leukocyte of the blood, to phagocytose and destroy small organisms, especially bacteria, which are present in the host. However, in neonates that have substantial deficiencies in the phagocytic system the ability for this system to effectively protect against bacterial invasion is severely impaired.

A second system of the immune system is the antibody-mediated immune system. This system utilizes immunoglobulins, such as antibodies, to circulate in the bloodstream and other body fluids, where they bind specifically to the foreign antigen that induced them. Binding of the antibody inactivates viruses and bacterial toxins by blocking their ability to bind receptors on target cells. Antibody binding also marks invading microorganisms for destruction, either by making it easier for a phagocytic cell (such as neutrophils) to ingest them or by activating a system of blood particles that kills the invader. The antibody-mediated immune system of healthy neonates is generally very immature and therefore is not truly effective in protecting neonates against bacterial infection at this early stage of life. In addition, the antibody-mediated immune system is only as effective as the neutrophil macrophage-phagocytic system since the antibody-mediated immune system depends on neutrophils to ingest and destroy all foreign particles tagged by the serum antibodies. Since the absolute neutrophil count (ANC) in neonates is naturally low, the antibody-mediated immunity system is also impaired. Those neonates in which their antibody-meditated immune system is even further compromised have virtually no antibody-mediated immune system at all and therefore depend solely on the neutrophil-macrophage phagocytic system to protect them against bacterial, fungal and viral infections.

Under normal conditions the production of neutrophils is increased under the influence of G-CSF. G-CSF is one of the hematopoietic growth factors that stimulates committed progenitor cells to proliferate and to form colonies of differentiating blood cells, preferentially neutrophils.

G-CSF has been found to be useful in the treatment of patients where the increase in neutrophils will provide additional protection from viral, fungal and bacterial infection. For example, U.S. Pat. No. 5,536,495 describes the use of G-CSF to reduce the occurrence of acute rejection as well as to reduce infections that are associated with organ transplants. Administering G-CSF to transplant patients has been successful in increasing the production of neutrophils in the blood, which in turn increased the patient's ability to ward-off infection.

Similarly, there is a need for a method of use for the administration of G-CSF to neutropenic neonates so as to enhance their immune systems by stimulating the production of neutrophils in the blood and/or causing the modulation of expression of effector cell molecules on the surface of the neutrophils.

Certain receptors which are present on the surface of neutrophils facilitate elimination of antibody-coated neonatal pathogens including bacteria and fungi through opsonization, enhanced chemotaxis and increased cytotoxic killing. Low levels of these receptors are thought to contribute to an increased susceptibility of sick VLBW neonates to infections with these organisms.

A method of using G-CSF to stimulate the production of neutrophils and/or modulate the production of the expression of effector cell molecules on neutrophils in neonates is desirable.

SUMMARY OF THE INVENTION

In accordance with the present invention, a method for enhancing the immune system in neonates by administering to neonates an amount of Granulocyte Colony Stimulating Factor (G-CSF) or a derivative thereof is provided. More particularly, the invention provides a method for enhancing neutrophil production and/or increasing the density of certain receptors on the surface of the neutrophils in Very Low Birth Weight (VLBW) neonates, pre-eclamptic neutropenic neonates, and/or septic-neutropenic neonates by administering an effective amount of (G-CSF) to the neonate. According to one preferred embodiment of the invention, G-CSF is administered in unit dosage of about 10 μg per kg of body mass in about 5% dextrose having a concentration of about 15 μg/ml of G-CSF over a one hour period daily for three days (up to 7 days) by microbore tubing with a maximum 0.8 ml dead space to limit drug loss on tubing.

DETAILED DESCRIPTION OF THE INVENTION

Figure 1:
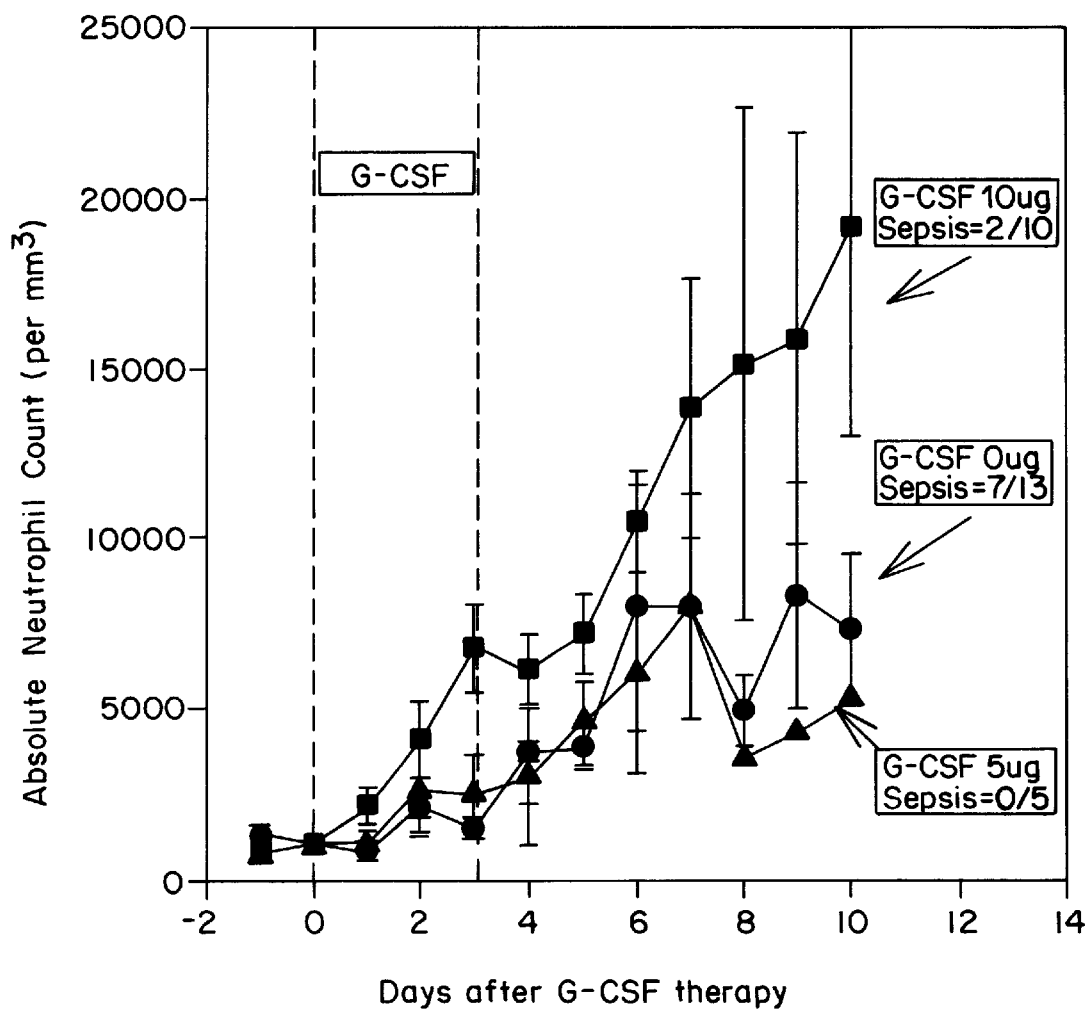
FIG. 1 graphically illustrates the neutrophil response following G-CSF therapy in Pre-eclampsia-Associated-Neutropenia.

According to the present invention, administering Granulocyte Colony Stimulating Factor (G-CSF) (available as NEUPROGEN® from Amgen Inc., Thousand Oaks, Calif.) to neonates results in a reduction in the rate of infection and improved overall survival rates of neonates. The invention also provides a method for enhancing neutrophil production in Very Low Birth Weight (VLBW) neonates, pre-eclamptic neutropenic neonates, and/or septic-neutropenic neonates by administering G-CSF to neonates suffering from these conditions. Both a pre-clinical study and a clinical study has been conducted on the affect of administering G-CSF to neonates.

The invention also provides a method for prophylaxis of sepsis in VLBW neonates and a method to enhance opsonization of infectious agents in neonates.

The term "G-CSF" as used herein is defined as naturally occurring human and heterologous species G-CSF, recombinately produced G-CSF (rhG-CSF) that is the expression product consisting of either 174 or 177 amino acids, or fragments, analogs, variants, or derivatives thereof as reported, for example in Kuga et al. Biochem. Biophy. Res. Comm 159: 103–111 (1989).

The preclinical study determined the effect of the surface expression of the $Fc_\gamma$ receptor and other complement receptors on neonatal neutrophils. Particularly, the surface expression of $Fc_\gamma$ RI(CD64), $Fc_\gamma$ RII(CD32), $Fc_\gamma$ RIII(CD16), CRI(CD35) and CR3(CD11b) on neutrophils may be affected by the administration of G-CSF. A preclinical study was conducted to measure the effect of G-CSF on the expression of the aforementioned receptors. The level of expression of each receptor was determined by indirect immunofluorescence using flow cytometry and monoclonal antibodies with a double labelling technique (FACS, Becton Dickson Flow Cytometer). It is believed that changes in the receptor density may affect neutrophil opsonization function and therefore reduce the average length of stay in which a neonate spends in the neonatal intensive care units. In addition, the clinical studies determined the affect of G-CSF on the ANC of neonates particularly neonates suffering from VLBW, pre-eclamptic neutropenia, and/or septic-neutropenia.

The clinical study determined the effect of G-CSF on the overall neutrophil production, as well as, the increase in surface expression of the $Fc_\gamma$ receptor and other complement receptors on neutrophils in neonates belonging to these three different groups.

The first group included neonates with neutropenia that have an absolute neutrophil count of less than 1500/mm$^3$. The neonates of this group are mostly associated with pregnancy induced hypertension (pre-eclampsia). The second group included neonates with Sepsis that have a positive blood culture plus some evidence of impaired blood flow or metabolic acidosis. The third group included neonates with Very Low Birth Weight (VLBW), weighing between 600 and 1300 grams at birth. These subjects have a high underlying risk of nosocomial infection due to their dysfunctional immune system. The demographic characteristics of the neonates included in the study are listed in table 1. The results and protocols of the study will be discussed below.

The Effect of G-CSF on $Fc_\gamma$ and Other Complement Receptors in Pre-clinical Trials.

To determine whether G-CSF could increase the density of $Fc_\gamma$ and complement receptors per cell, as well as the absolute number and percentage of neutrophils expressing this phenotype, G-CSF was administered to nine pre-eclampsia associated neonatal neutropenia, eight sepsis associated neutropenia and seven neonates with normal neutrophil counts. Twenty-four neonates were treated intravenously with about 10 μg/kg/d in about 5% dextrose having a final concentration of about 15 μg/ml of G-CSF over a one hour period daily for a maximum of three days via a microbore tubing with a 0.8 ml dead space to limit drug loss on tubing. Surface expression of the above mentioned receptors were studied at day 0, day 3, day 7 and day 28 following G-CSF administration. Flow cytometry was performed before and again at three days and seven days after initiating G-CSF treatment in conjunction with conventional neonatal management: antibiotics, pressors and ventilation support.

The mean fluorescent intensity of $Fc_\gamma$ RI receptors increased in all groups. The $Fc_\gamma$ RIII receptors percentage increased in pre-eclampsia and pre-term neonates after the administration of G-CSF, but not in the septic neonates. Neutropenic neonates of pre-eclamptic women responded by increasing their ANC by eight and seventeen fold at three and seven days. $Fc_\gamma$ I, $Fc_\gamma$ II, CRI and CR3 increased at day three, where as $Fc_\gamma$ III increased only by day seven. In sharp contrast, the septic neonates showed a decrease in receptor density per cell despite a thirty fold increase in neutrophil cell number.

The findings listed above indicate that intravenous administration of G-CSF modulates the expression of effector cell molecules on circulating neutrophils in neonates of pre-eclamptic women, as well as in pre-term neonates. The decrease in receptor density despite the thirty-fold increase in neutrophil cell production may indicate that the high mortality rate associated with septic neonates may be due to a blocking in the mechanism responsible for producing these receptors or possibly the down regulation of the receptors.

Overall the administration of G-CSF to neonates concurrently with conventional treatments modulate the expression of effector cell molecules on neutrophils and therefore increase the effectiveness of circulating neutrophils in the bloodstream of neonates.

The Effect of G-CSF on the Absolute Neutrophil Count (ANC) in Neonates.

To determine whether G-CSF could increase the overall neutrophil production G-CSF was administered to neonates with Neutropenia, Sepsis, or Very Low Birth Weight (VLBW) without neutropenia.

The neonates with neutropenia had ANC of less than 1500/mm$^3$ which were identified in two separate peripheral blood samples taken twelve hours apart. The ANC were determined by multiplying the total leukocyte count (corrected for nucleated red bloods cells obtained by Coulter Counter, model #STKS) by the percentage of polymorphonuclear leukocytes and band forms identified manually in peripheral venous or arterial blood. It should be noted that metamyelocyte and myelocyte were not included because they may not be functionally active as a phagocytic defense system and contribute minimally to the total count.

The neonates with sepsis had a positive blood culture plus some evidence of impaired blood flow or metabolic acidosis. In addition, the septic neonates had at least one of the following ailments: respiratory distress; apnea; temperature instability; or other well accepted clinical signs of sepsis. The neonates that were included in the clinical trials were in a neutropenic state for greater or equal to 24 hours and have an unexplained metabolic acidosis (greater than 5 meq/l). Finally, the neonates with Very Low Birth Weight (VLBW) weighed between 600 and 1300 grams at birth.

The total number of neonates involved in the study was 25, and were divided into a study group and a control group. The study group included 14 of the 25 neutropenic septic neonates and was compared to the control group which contained the remaining eleven neutropenic septic neonates.

Both the study population and the control population were managed with appropriate conventional therapeutic interventions including antibiotics, oxygen and mechanical ventilatory support, intravenous fluids, vasopressor drugs (dopamine or dobutamine) and other standard interventions deemed necessary by the attending neonatologist responsible for the clinical management of the neonate independent of the drug therapy. Individuals in the study group received intravenous G-CSF (Filgrastin; Amgen, Thousand Oaks, CA) at a dose of about 10 µg/kg/d in 5% dextrose (final concentration about 15 µg/ml) over one hour periods daily for a maximum of three days administered via microbore tubing (0.8 ml dead space to limit drug loss on tubing). The control group included the remaining eleven neutropenic septic neonates each of which were concurrently treated using only conventional therapy.

The absolute neutrophil count at the time of entry into this protocol of the G-CSF study group was 585±138/mm$^3$ (mean±SEM) and 438±152/mm$^3$ (p-ns) in the conventionally managed group as listed in table 2. The ANC increased by 7-fold vs 2-fold at 24 hours after entry into the study protocol in the G-CSF and conventional treatment groups respectively. Subsequently, the ANC was increased by 13-fold vs 4-fold at 48 hrs, 21-fold vs. 5-fold at 72 hrs. and 27-fold vs. 16-fold at 7- to 10 days after entry in G-CSF and conventional treatment groups respectively.

All but one patient with an ANC of zero (who expired <24 hrs after entry into the protocol), showed a statistically significant response to G-CSF that persisted at 72 hrs and peaked between 7- to 10 days after the last dose of G-CSF was administered. In stark contrast, conventionally managed patients had ANC's that were consistently lower than the G-CSF group on all days after entry into this protocol and were only significantly increased at the 7–10 day point as shown in table 2 and FIG. 1.

Table 2 lists the conventional group having 13 patients, a study group that received 5 µg of G-CSF in 5% dextrose (alternatively 0.2% albumin can be added if a lower final concentration below 15 µg/ml is used) intravenously via microbore tubing having a 0.8 ml dead space to limit drug loss contained 5 patients and a study group that received about 10 µg of G-CSF in about 5% dextrose intravenously via microbore tubing having a 0.8 ml dead space to limit drug loss contained 10 patients. In the table, the number of neonates in each group that tested positive for different bacterial strains are listed. In addition, the table list the death rate within 28 days of treatment and after 28 days of treatment. As shown in table 2, three neonates expired prior to the 28th day of treatment and one neonate expired after the 28th day of treatment in the conventional group; one neonate expired prior to the 28th day of treatment and one neonate expired after the 28th day of treatment in the study group that received about 5 µg of G-CSF; and one neonate expired prior to the 28th day of treatment and three neonates expired after the 28th day of treatment in the study group that received about 10 µg of G-CSF.

In addition, about 0.5 gm of intravenous gamma globulin (IVGG) per kilogram of body mass per day can be used with interventional or prophylactic use of G-CSF in order to enhance opsonization of infections in neonates.

FIG. 1 graphically shows the neutrophil response following G-CSF therapy in pre-eclampsia-associated-neutropenia. The graph compares the "absolute neutrophil count" with the "days after G-CSF therapy." FIG. 1 contains three lines. The line with the darkened circles illustrates the effect on the ANC when no G-CSF is administered, the line with the darkened triangles illustrates the affect on the ANC when about a 5 µg dosage of G-CSF in about 5% dextrose was intravenously administered and the darkened squares illustrate the affect on the ANC when about a 10 µg dosage of G-CSF in about 5% dextrose is intravenously administered. In each case G-CSF was administered within the first three days from the inception of the study. As can be seen from the graph, the 5 µg G-CSF and the 0 µg G-CSF lines show minimal increase in the ANC over 10 days, while the 10 µg G-CSF line indicates a sharp increase over 10 days. The 10 µg G-CSF line shows an increase in ANC from about 1000 neutrophils per mm$^3$ to about 19,000 neutrophils per mm$^3$. This indicates that a 10 µg dosage of G-CSF in 5% dextrose administered intravenously to neonates suffering from pre-eclampsia-associated-neutropenia elicits a considerable increase in the ANC in those neonates. Therefore, administering a 10 µg dosage of G-CSF in 5% dextrose intravenously by a microbore tubing having a 0.8 ml dead space to neonates increases the ANC and may increase the survival rate of neonates suffering from the aforementioned diseases.

The invention also includes a method for prophylaxis of sepsis in VLBW neonates which comprises administering 10 µg per kilogram of body mass per day of G-CSF intravenously for about three consecutive days each week for about a four week period to reduce the risk of infection.

Finally, the above-discussion is intended to be merely illustrative of the invention. Numerous alternative embodiments may be devised by those having ordinary skill in the art without departing from the spirit and scope of the following claims.

TABLE 1

Demographic Characteristics of Study Population

|  | Conventional (n = 13) | rhG-CSF 5 ug (n = 5) | rhG-CSF10 ug (n = 10) |
|---|---|---|---|
| Birth weight (grams) | 732 ± 85<br>356–1100<br>670 | 824 ± 104<br>579–1210<br>805 | 802 ± 56<br>536–1130<br>780 |
| Gestational age (weeks) | 28 ± 1<br>26–32<br>27 | 28 ± 1<br>25–31<br>28 | 27 ± 1<br>24–30<br>28 |
| Sex (M/F) | 8/5 | 4/1 | 8/2 |
| Growth retardation | 5 | 3 | 8 |
| Cesarian delivery | 9 | 4 | 9 |
| 5 Min APGAR < 3 | 1 | 0 | 0 |
| RDS | 13 | 5 | 10 |
| Surfactant use | 11 | 4 | 8 |
| UAC | 11 | 4 | 8 |
| UVC | 8 | 4 | 6 |
| PICC | 12 | 3 | 9 |

Note: numbers represent the number of patients with each item unless otherwise indicated. Growth retardation = <10%'ilc for weight (****), UAC = umbilical arterial catheter, UVC = umbilical venous catheter, PICC = percutanous intravenous central venous catheter.

TABLE 2

Neonatal Outcome Measures

|  | Conventional (n = 13) | rhG-CSF 5 ug (n = 5) | rhG-CSF10 ug (n = 10) |
|---|---|---|---|
| Sepsis | 7 | 0 | 2 |
| E. coli | 1 | 0 | 0 |
| S. epi | 2 | 0 | 2 |
| Pseudomonas | 2 | 0 | 0 |
| Serratia | 2 | 0 | 0 |
| NEC | 1 | 0 | 1 |
| BPD | 9 | 2 | 6 |
| Death (<28d) | 3 | 1 | 1 |
| Death (>28d) | 1 | 1 | 3 |

NEC: Necrotizing enterocolitis was diagnosed when abdominal distension, bilious gastric drainage, gross blood in the stools and radiological evidence of pneumatosis intestinalis were observed (***),
BPD: Bronchopulmonary dysplasia was diagnosed if a neonate required oxygen >28 days after birth and had associated radiographic findings as determined by a board certified radiologist (****).

What is claimed is:

1. A method for enhancing opsonization of infectious agents in neonates comprising:

administering an effective amount of recombinant human Granulocyte Colony Stimulating Factor (rhG-CSF) to neonates, wherein rhG-CSF is intravenously administered to sepsis-associated neutropenic neonates.

2. The method of claim 1 wherein about 10 µg per kilogram of body mass per day of rhG-CSF is intravenously administered in the form of a solution comprising about 5% dextrose and having a fixed concentration of about 15 µg/ml of rhG-CSF to septic neutropenic neonates over a one hour period daily for a maximum of three days by microbore tubing with a maximum 0.8 ml dead space to limit drug loss on tubing.

3. A method for prophylaxis of sepsis in Very Low Birth Weight (VLBW) neonates by enhancing the number of neutrophils and by enhancing opsonization of infectious agents wherein about 10 µg per kilogram of body mass per day of recombinant human Granulocyte Colony Stimulating Factor (rhG-CSF) is intravenously administered for about three consecutive days each week for about a four week period to reduce the risk of infection.

4. The method of claim 3 further comprising administering about 0.5 gm intravenous gamma globulin (IVGG) per kilogram of body mass per day in order to enhance opsonization of infectious agents in neonates.

* * * * *